United States Patent
Guenin et al.

(10) Patent No.: US 7,011,822 B2
(45) Date of Patent: *Mar. 14, 2006

(54) EFFECTIVE SOFT SOLID PERSONAL CARE PRODUCT

(75) Inventors: Eric Guenin, Pennington, NJ (US); Jairajh Mattai, Piscataway, NJ (US); John Afflitto, Brookside, NJ (US); John Hogan, Piscataway, NJ (US); John Jonas, Summit, NJ (US); Wilson Lee, Bloomfield, NJ (US); Elizabeth Linn, Lyndhurst, NJ (US); Rosemary Munsayac, West Orange, NJ (US); Xiaozhong Tang, Bridgewater, NJ (US); Kathy Potechin, Short Hills, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/349,857

(22) Filed: Jan. 23, 2003

(65) Prior Publication Data

US 2004/0028628 A1    Feb. 12, 2004

Related U.S. Application Data

(63) Continuation-in-part of application No. 10/267,544, filed on Oct. 9, 2002, which is a continuation-in-part of application No. 09/671,775, filed on Sep. 28, 2000, now abandoned.

(60) Provisional application No. 60/194,462, filed on Apr. 4, 2000.

(51) Int. Cl.
| A61K 7/32 | (2006.01) |
| A61K 7/34 | (2006.01) |
| A61K 7/36 | (2006.01) |
| A61K 7/38 | (2006.01) |
| A61K 31/74 | (2006.01) |

(52) U.S. Cl. .......... 424/65; 424/400; 424/401; 424/66; 424/67; 424/68; 424/78.02; 424/78.08

(58) Field of Classification Search ......... 424/400, 424/401, 65, 66, 67, 68, 78.02, 78.08
See application file for complete search history.

(56) References Cited

U.S. PATENT DOCUMENTS

| 5,178,881 A | * | 1/1993 | Mackles et al. ............ 424/489 |
| 5,942,215 A | * | 8/1999 | Edwards et al. ............ 424/65 |
| 6,511,658 B1 | * | 1/2003 | Mattai et al. .............. 424/65 |

FOREIGN PATENT DOCUMENTS

| WO | WO 98/18438 A1 * | 5/1998 |
| WO | WO 99/51192 A2 * | 10/1999 |

OTHER PUBLICATIONS

ACUMIST B-18 Product Details, Honeywell, 2002.*

* cited by examiner

*Primary Examiner*—Sreeni Padmanabhan
*Assistant Examiner*—Marina Lamm
(74) *Attorney, Agent, or Firm*—Kristyne A. Bullock

(57) ABSTRACT

A low residue antiperspirant and/or deodorant composition in the form of an anhydrous, surfactant-free and antiseptic alcohol-free suspension exhibiting a syneresis of less than 8% which is made by combining selected amounts of: (a) a cyclomethicone (and) dimethicone crosspolymer made with an ≡Si—H containing polysiloxane and an alpha, omega-diene of formula $CH_2=CH(CH_2)_xCH=CH_2$ which crosspolymer has a viscosity in the range of 50,000–3,000,000 centipoise, preferably with a nonvolatiles content of 10–14% in cyclomethicone; (b) polyethylene beads having a density in the range of 0.91–0.98 grams/cm$^3$ and a particle size in the range of 5–40 microns; (c) a volatile silicone; (d) an emollient (or a mixture of two or more emollients) which may include a non-volatile silicone and an additional amount of a volatile silicone; and (e) an effective amount of an antiperspirant active material in an amount sufficient to have an antiperspirant and/or a deodorant effect.

12 Claims, No Drawings

US 7,011,822 B2

EFFECTIVE SOFT SOLID PERSONAL CARE PRODUCT

This application is a continuation-in-part of U.S. Ser. No. 10/267,544, filed Oct. 9, 2002, which itself is a continuation-in-part of U.S. Ser. No. 09/671,775, filed on Sep. 28, 2000, now abandoned, which itself claims priority from provisional case 60/194,462 filed on Apr. 4, 2000, under 35 U.S.C. 119(e).

FIELD OF THE INVENTION

This invention relates to soft solid products made as suspensions and suitable for use as antiperspirants and/or deodorants.

BACKGROUND OF THE INVENTION

There is a continuing trend to develop new and superior cosmetic compositions especially for the reduction and/or elimination of wetness and/or odor under the arms.

Particular efforts include developing lower residue products especially with improved efficacy and aesthetics. Various product forms have included sticks (especially gel/sticks), gels, soft solids, roll-ons, aerosols and creams. Of these various forms the sticks, gels, soft solids creams and roll-ons are made with a liquid base material incorporating a solidifying agent and/or gelling agent and/or thickening agent. Generally, these forms include a solution of the cosmetically active ingredient in a suitable vehicle, a suspension of the active ingredient in a carrier vehicle, or a multiphasic dispersion or emulsion in which a solution of the active ingredient is dispersed or suspended in some continuous phase or in which the solubilized active ingredient constitutes the continuous phase.

A variety of soft-solid formulations are known. These include formulations made with the following ingredients:

(a) clay thickening agent and an activator for the clay: for example, U.S. Pat. No. 5,019,375 to Tanner et al; and U.S. Pat. No. 4,526,780 to Marschner et al;

(b) particulate thickening agents such as fumed silica: for example, U.S. Pat. No. 5,069,897 to Orr; and U.S. Pat. No. 4,937,069 to Shin;

(c) selected volatile and/or non-volatile alkylmethylsiloxanes such as those including a structuring wax: for example, U.S. Pat. No. 5,225,188 to Abrutyn et al; and PCT applications WO 97/16161 and 16162 both of which are assigned to Unilever PLC; and (d) triglyceride gellants such as the glyceryl tribehenate described in U.S. Pat. No. 5,718,890 to Putnam et al.

The use of a class of compositions known as silicone elastomers in cosmetic compositions has shown some interesting results. PCT case WO 97/44010 and assigned to the same assignee as this application describes a silicone gel material made by combining (a) a volatile silicone material and (b) an organopolysiloxane material (or silicone elastomer) as a gelling agent wherein the organopolysiloxane material (silicone elastomer) can be a reaction product of a vinyl-terminated siloxane polymer and a silicon hydride cross-linking agent. Related technology is also disclosed in PCT case WO 98/00097, WO 98/00104 and 98/00105 assigned to Unilever PLC on cross-linked non-emulsifying elastomers.

U.S. Pat. No. 5,599,533 to Stepniewski et al assigned to Estee Lauder describes a stable water-in-oil emulsion system formed with an organopolysiloxane elastomer, a vehicle in which the elastomer is dispersed or dispersible, a stabilizing agent, a surfactant and an aqueous component. A commercial product known as "REVELATION" retexturizing complex for hands and chest sold by the same assignee contains a silicone gel material with an organopolysiloxane component and octamethylcyclotetrasiloxane.

EP 0 787 758 A1 teaches a method for solvent thickening by using a silicone latex having a plurality of crosslinked polysiloxane particles.

Another recent case assigned to the same assignee as this application is WO 99/51192 and U.S. patent application Ser. No. 9/273,152 which describes antiperspirant compositions with the use of broad categories of elastomers. Other examples of the use of elastomer type materials and/or methods for processing such materials may be found in PCT cases WO 98/00097; WO 98/00104; WO 98/00105; WO 98/18438; WO 98/42307 all of which are incorporated herein by reference.

Two major problems have been observed when the use of elastomer materials is included in soft solid formulations. The first problem is reduction in efficacy due to the formation of an occlusive elastomeric film which prevents the active from diffusing into the sweat duct. The second problem is the consistency of the product as evidenced by high viscosity and elastic behavior when applied to the surface of the skin. In order to reduce this high viscosity, emollients and solvents have to be added which may negatively impact efficacy of the deodorant and/or antiperspirant. It has been found that the use of a selected type of elastomer in soft solid formulations in combination with polyethylene beads as described herein overcomes these problems.

In addition, the formula of the present case excludes the presence of a surfactant for example, those having an HLB value in the range of 8–16 as described in WO 99/51192, owned by the same entity as this case.

Thus, it is an object of the invention to provide improved cosmetic compositions with the improvements as previously described and which are useful as antiperspirants and/or deodorants. These and other objects of the invention will be apparent from the following description of the invention.

SUMMARY OF THE INVENTION

It has been found that an improved surfactant-free, soft solid cosmetic product may be made as a suspension formed with:

(a) a cyclomethicone (and) dimethicone crosspolymer made with an $\equiv$Si—H containing polysiloxane and an alpha, omega-diene of formula $CH_2\!=\!CH(CH_2)_xCH\!=\!CH_2$, where x=1–20, to form a gel by crosslinking and addition of $\equiv$Si—H across double bonds in the alpha, omega diene, which crosspolymer has a viscosity in the range of 50,000–3,000,000 centipoise (particularly 100,000–1,000,000; more particularly 250,000–450,000 centipoise; and most particularly 350,000 centipoise), preferably with a nonvolatiles content of 8–18% (particularly 10–14% and most particularly 12–13%) in cyclomethicone (for example a D4 or D5 cyclomethicone), (an example of such a crosspolymer composition being DC-9040 from Dow Corning Corporation (Midland, Mich.) with other types of such crosspolymers (also called elastomers) being described in U.S. Pat. No. 5,654,362, incorporated by reference herein as to the description of such polymers and methods of making such polymers);

(b) polyethylene beads having a density in the range of 0.91–0.98 grams/cm$^3$ and a particle size in the range of 5–40 microns, wherein the polyethylene beads are used in an amount of at least 2% by weight based on the total weight of the composition;

(c) a volatile silicone;

(d) an emollient (or a mixture of two or more emollients) which may include a non-volatile silicone and an additional amount of a volatile silicone; and (e) an effective amount of an antiperspirant active material in an amount sufficient to have an antiperspirant and/or a deodorant effect.

The soft solid antiperspirant and/or deodorant product of this invention is an opaque product which leaves little or no white residue when applied and which exhibits improved efficacy and stability as compared to other formulations with different types of elastomers. Reduction of sweat of at least 40% can be achieved with the compositions of the invention as compared to typical levels of 15% for other products.

DETAILED DESCRIPTION OF THE INVENTION

The compositions of this invention are low residue antiperspirant and/or deodorant products which are anhydrous, surfactant-free and antiseptic alcohol-free suspensions, particularly those which exhibit a syneresis of less than 8%. The stable, high efficacy, surfactant free and antiseptic alcohol-free low residue compositions of this invention are made by combining:

(a) 40–75% (particularly 45–60%, and, more particularly, 46–53%) of a volatile silicone (especially a D5 cyclomethicone);

(b) 1–20% (particularly 2–18% and, more particularly, 5–15%) of an emollient or a mixture of two or more emollients (for example, 0.1–5% (particularly 0.3–4.0%, more particularly 0.4–2.0% and even more particularly 0.4–1.5%) of a non-volatile silicone such as phenyltrimethicone; or 1–12% C12–15 alkyl benzoate);

(c) 1–10% (on a solids basis) (for example, 6.00–6.76%, 6.0–6.5% or 5.64–6.82%) of the cyclomethicone (and) dimethicone crosspolymer composition as described above;

(d) 0.1–20% (particularly 10–20% to get an antiperspirant effect) of an antiperspirant active based on an anhydrous, buffer-free antiperspirant active;

(e) 2–15% (particularly 2–10% and, more particularly, 2–8%) of polyethylene beads having a particle size in the range of 5–40 microns and a density in the range of 0.91–0.98 g/cm$^3$;

(f) 0–5% antimicrobial agent; and (g) 0–5% fragrance;

wherein (1) all percents are in percents by weight based on the total weight of the composition unless otherwise indicated; (2) the composition exhibits a syneresis of less than 8%; and (3) the composition is subjected to a homogenizing process after the ingredients are combined.

By anhydrous is meant no added water. It is anticipated that any waters of hydration in the antiperspirant salt would give a water content of the entire composition of less than 7.5 weight %.

The silicone materials used in forming the compositions of the present invention may be selected from the group consisting of conventional cyclic and linear volatile and non-volatile silicones which act as a swelling agent for the suitable elastomer. Illustratively, and not by way of limitation, the volatile silicones are one or more members selected from the group consisting of cyclic polydimethylsiloxanes such as those represented by Formula I:

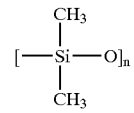

Formula I where n is an integer with a value of 3–7, particularly 5–6. By volatile silicone material is meant a material that has a measurable vapor pressure at ambient temperature. For example, DC-245 fluid from Dow Corning Corporation (Midland, Mich.) is a type of cyclomethicone which can be used. These include a tetramer (or octylmethylcyclotetrasiloxane) and a pentamer (or decamethylcyclopentasiloxane). The nonvolatile and volatile linear silicones are one or more members selected from the group consisting of linear polydimethylsiloxanes such as those represented by Formula II:

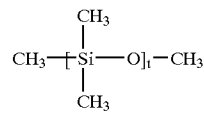

Formula II and t is selected so that the molecular weight ranges from 800–260,000 and the viscosity ranges from 5–600,000 centistokes, for example Dimethicone DC 200 from Dow Corning.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula III:

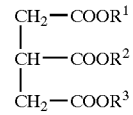

Formula III wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO—OR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^6COOH$ with the $R^6$ group having a carbon chain length between 7 and 30, straight chain or branched. Specific examples include lauric, myristic, palmitic, stearic, oleic, linoleic and behenic acid.

(e) saturated and unsaturated fatty alcohols (including guerbet alcohols) with general structure $R^7CH_2OH$ where $R^7$ can be straight or branched and have carbon length of 7 to 30. Specific examples include lauryl, myristyl, cetyl, isocetyl, stearyl, isostearyl, oleyl, ricinoleyl and erucyl alcohol;

(f) lanolin and its derivatives which are a complex esterified mixture of high molecular weight esters of (hydroxylated) fatty acids with aliphatic and alicyclic alcohols and sterols. General structures would include $R^8CH_2—(OCH_2CH_2)_nOH$ where $R^8$ represents the fatty groups derived from lanolin and n=5 to 75 or $R^9CO—(OCH_2CH_2)_nOH$ where $R^9CO—$ represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(g) alkoxylated alcohols wherein the alcohol portion is selected from aliphatic alcohols having 2–18 and more particularly 4–18 carbons, and the alkylene portion is selected from the group consisting of ethylene oxide, and propylene oxide having a number of alkylene oxide units from 2–53 and, more particularly, from 2–15. Specific examples include PPG-14 butyl ether, PPG-53 butyl ether, and PPG-3 myristyl ether.

(h) silicones and silanes which are organo-substituted polysiloxanes which are selected from polymers of silicon/oxygen having general structures:

(1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl;

(2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl; or (3) organo substituted silicon compounds of formula $R^{17}Si(R^{18})OSiR^{19}$ which are not polymeric where $R^{17}$, $R^{18}$ and $R^{19}$ can be the same or different and are each independently selected from the group consisting of phenyl and C1–C60 alkyl optionally with one or both of the terminal R groups also containing an hydroxyl group. Specific examples include dimethicone (for example, dimethicone having a viscosity of 0.5–1.5 centistokes), dimethiconol behenate, $C_{30-45}$ alkyl methicone, stearoxytrimethylsilane, phenyl trimethicone and stearyl dimethicone.

(i) mixtures and blends of two or more of the foregoing.

Emollients of special interest include C12–15 alkyl benzoate (FINSOLV TN from Finetex Inc., Elmwood Park, N.J.); phenyltrimethicone, isopropyl myristate; and neopentyl glycol diheptanoate.

The emollient or emollient mixture or blend thereof incorporated in compositions according to the present invention can, illustratively, be included in amounts of 0.5–50%, preferably 1–25%, more preferably 3–12%, by weight, of the total weight of the composition.

One particular elastomer of interest is DC-9040 from Dow Corning Corporation.

One particular range of cyclomethicone (and) dimethicone crosspolymer compositions based on the Examples described below is 6.00–6.76% (solids). Another particular range based on the Examples below is 6.0–6.5% (solids). A third particular range based on the Examples below is 5.64–6.82% (solids). These Examples generally use about 12–13% elastomer (solids) in a cyclomethicone such as D5 cyclomethicone.

The antiperspirant active can be selected from the group consisting of any of the known antiperspirant active materials. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Particular types of antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.); Westchlor 30BDM XF (from Westwood Chemical Co., Middletown, N.Y.). Particular tetrachlorohydrex salts include AZP 902 SUF from Reheis and Westchlor 35BDM XF from Westwood. Any of these salts can be processed to obtain 98% of the particles less than 10 microns in size; 95% of the particles less than 10 microns in size; 90% of the particles less than 10 microns in size; or 85% of the particles less than 10 microns in size.

Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein. Particular actives include Westchlor A2Z 4105 aluminum zirconium tetrachlorohydrex gly propylene glycol complex, (from Westwood Chemical Corporation, Middletown, N.Y.); Westchlor ZR 35B aluminum zirconium tetrachlorhydrex gly, and Rezal 36 GP and AZP 902 aluminum zirconium tetrachlorhydrex gly both from Reheis, Berkeley Heights, N.J. as well as Rezal AZZ 908 from Reheis. In general, the metal:chloride mole ratio is in the range of 2.1–0.9:1 for such salts.

Actives of special interest because they form low RI solutions include: Westchlor Zr 35BX3 (30–35% actives in water) from Westwood Chemical Company, Middletown, N.Y.; Rezal 36G (46% in water) from Reheis Inc., Berkeley Heights, N.J.; Summit AZG-368 (28–32% in water) from Summit Research Labs, Huguenot, N.Y.; Reach 301 (39% in water) from Reheis Inc.; and aluminum chloride (28% in water) which may be obtained from several sources. In general, the metal:chloride mole ratio is approximately 1.4:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1.

Antiperspirant actives can be incorporated into compositions according to the present invention in amounts in the range of 0.1–25% of the final composition, but the amount used will depend on the formulation of the composition. For example, at amounts in the lower end of the broader range (for example, 0.1–10% on an actives basis), a deodorant effect may be observed. At lower levels the antiperspirant active material will not substantially reduce the flow of perspiration, but will reduce malodor, for example, by acting as an antimicrobial material. At amounts of 10–25% (on an actives basis) such as 15–25%, by weight, of the total weight of the composition, an antiperspirant effect may be observed.

The antiperspirant active material is desirably included as particulate matter suspended in the composition of the present invention in amounts as described above, but can also be added as solutions or added directly to the mixture.

The polyethylene beads useful with this invention have a density in the range of 0.91–0.98 g/cm$^3$ and a particle size in the range of 5–40 microns, with one particular type of polyethylene having a particle size of 20 microns. All particle sizes are averages. Several types of suitable polyethylene beads that are commercially available are MICROTHENE FN 510 from Equistar Chemicals LP (Houston, Tex.); ACUMIST A-6 from Allied Signal Corp., Morristown, N.J.).), and Performalene™ (New Phase Technology, Piscataway, N.J.). The polyethylene component contributes to the reduction in syneresis and is also responsible for giving the products a powdery feel as determined by trained sensory panels.

Suitable antimicrobial agents include, for example, bacteriostatic quaternary ammonium compounds such as 2-amino-2-methyl-1-propanol (AMP), cetyl-trimethylammonium bromide, cetyl pyridinium chloride, 2, 4, 4'-trichloro-2'-hydroxydiphenylether (Triclosan), N-(4-chlorophenyl)-N'-(3,4-dichlorophenyl)urea (Triclocarban), silver halides, octoxyglycerin (Sensiva™ SC 50) and various zinc salts (for example, zinc ricinoleate). The bacteriostat can, illustratively, be included in the composition in an amount of 0–5%, particularly 0.01–1.0% by weight, of the total weight of the composition. Triclosan, can illustratively be included in an amount of from 0.05% to about 0.5% by weight, of the total weight of the composition.

A variety of fragrances can be used in these compositions if a scented products is desired. Fragrances can be used in an amount in the range of 0–5%, particularly 0.01–2.0%, and, for example, at a level of 1%.

Masking agents can be used in an amount of 0.05–5.0% (particularly 0.05–2%) by weight based on the total weight of the composition if an unscented product is desired.

Other various optional components include those described in U.S. Pat. No. 5,019,375 to Tanner et al; U.S. Pat. No. 4,937,069 to Shin; and U.S. Pat. No. 5,102,656, each of which is incorporated by reference in its entirety herein. Examples of such additional ingredients include fragrances, coloring agents, soothing agents (such as aloe and its derivatives), opacificers, etc. in types and amounts conventionally used for such products, some of which have already been described above.

These compositions are soft solids made as suspensions and thickened or gelled to obtain the desired viscosity. Viscosity may be modified by using various types and amounts of (1) elastomer; (2) antiperspirant active (for example, selected on the basis of physical properties such as particle size, surface area, moisture content, loss on drying and/or oil adsorption); (3) polyethylene beads (for example, selected on the basis of physical properties such as particle size, surface area, etc.). Viscosity may also be varied by using processing techniques on the final product such as homogenization. The optimum viscosity will depend on the type of packaging used as the delivery system and the size of the openings. A viscosity will be selected to give the appropriate payout under normally exerted pressure and still minimize leakage. While thickening may be achieved in several ways, the compositions of this invention will normally use the elastomer component as the gellant. Of course various viscosities for a soft solid may be made depending on the amount of elastomer material and the amount of other ingredients used. One group of products having a more viscous form will have a viscosity in the range of 50,000–2,500,000 (particularly 50,000–1,000,000 centipoise) and will be suitable for use with an applicator with porous openings or slots such as those described in U.S. Ser. No. 9/191,897 (PCT 99/25570) incorporated by reference herein as to the description of the applicators. Another form will have a lower viscosity such as in the range of 20,000–200,000 centipoise and will be suitable for use with applicators requiring a thinner composition, for example roll-on applicators which have a rolling ball structure. For example, such roll-on applicators are described in U.S. Pat. Nos. 5,158,385 and 4,984,921. incorporated by reference herein as to the description of the applicators.

While various forms have been described, it is believed that the compositions made according to this inventions should preferably have a ratio of elastomer to antiperspirant active in the range of 1:2–1:20 in order to achieve the optimum improved efficacy and the improved stability that has been observed.

Compositions according to the present invention can be made by mixing the silicone gel material with active ingredient(s) and optionally one or more of emollient(s), thickener(s) and fragrance. Mixing conditions and the use of heating will depend on what types of materials are being combined and the melting points for those materials as are known to those skilled in the art. For example if soft solids, roll-ons or gels are being made, temperatures, in the range of room temperature or slightly higher (for example, 25–50 degrees C., particularly 23–30 degrees C.) may be used. For stick products and soft solid/cream products made with higher melting point materials (for example, high temperature waxes) temperatures from 25–85 degrees C. may be used. The mixture can be introduced into dispensing containers known to those skilled in the art including those for solids, gels, roll-ons, soft solids and creams. In one particular example, slotted dispensers may be used such as those known in the art, for example, those having a parallel row or rows of straight or curved slots or holes with a screw mechanism for forcing the composition through the top as the product is used.

Where the dispensing containers have a top surface with slots therein, the composition can be rubbed onto the skin from the top surface of the container (itself fed from a reservoir of product in the container) so as to deposit an adequate amount of the cosmetic composition on to the skin. The cosmetic composition, for example, an antiperspirant and/or deodorant in the form of a soft solid, can be extruded from inside the dispensing container through the slots or holes onto the top of the surface of the dispensing container, and from there may be applied to the skin in the axillary regions to deposit sufficient amounts of antiperspirant and/or deodorant active material to reduce body malodor and/or reduce perspiration in axillary regions of the human body.

Various forms of the invention can be exemplified by the following formulations but should not be construed as limitations on the invention:

Soft Solid
(a) 1–20% of a volatile silicone such as D4 or D5 cyclomethicone (or mixtures thereof);
(b) 1–20% of an emollient component comprising 0–12% (particularly1–8%) of FINSOLV TN C12–15 alkyl benzoate; 0–8% (particularly 0.5–5%) (more particularly, 0.3–5%) neopentyl glycol diheptanoate; 0–2% (particularly 0.5–2%) (more particularly, 0.3–2%) isopropyl myristate; 0–1.5% (particularly 0.4–1.5%) (more particularly 0.3–1.5%) of a non-volatile silicone such as phenyltrimethicone;
(c) 40–60% elastomer composition in cyclomethicone (particularly above 47%) (for example, DC-9040);
(d) 15–25% antiperspirant active;
(e) 3–10% polyethylene beads of the type described above; and
(f) optionally 0.5–1.5% fragrance.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application (a) values for n, m, etc. in formulas, molecular weights and degree of ethoxylation or propoxylation are averages; (b) temperatures are in degrees C. unless otherwise indicated; and (c) the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). Mixing techniques used to make the compositions are those conventionally used in the art including those described above.

Example 1

General Method #1 of Making Compositions

The solvent components such as the volatile silicone (for example, cyclomethicone), emollients (such as non-volatile silicone (for example, phenyltrimethicone), C12–15 alkyl benzoate, neopentyl glycol diheptanoate and isopropyl myristate) are added to a large capacity mixer equipped with a mechanical stirrer and blended for about 5 minutes or until a homogeneous dispersion is formed. The antiperspirant active is then added as a dry powder with continuous mixing followed by the polyethylene beads. The entire mixture is mixed for about 20 minutes or until a homogeneous dispersion is formed. The sides of the mixing vessel are scraped with a spatula of sufficient size to free solid chunks of particulates. The elastomer is then added and blending is continued for about 20 minutes or until a homogeneous white creamy paste is formed. If fragrance is added it is done so at this point and mixed until well blended or for about 5 minutes. The resulting soft solid is then passed through a homogenizer (KINEMATIC homogenizer) and placed back into the reaction vessel. Multiple passes through the homogenizer are used (usually about 1–4) until the product is stable, that is, exhibits a syneresis of less than 8%, and preferably less than 5% as evaluated by the process described in Example 5, below. The final product may be placed in suitable packaging with openings that accommodate the viscosity of the final product. The entire process may be done without the application of any additional heat. If, however, a component is used which requires melting, the premelting of this component will be required.

Example 2

General Method #2 of Making Compositions

The elastomer composition is weighed out in a stainless steel container, which container is part of a Hobart Mixer (Model N-50, from Hobart Corporation, Troy, Ohio). The cyclomethicone, dimethicone, neopentyl glycol diheptanoate, diethyl phthalate and isopropyl myristate are weighed separately and added sequentially to the same container as the elastomer. The ingredients are blended for about 5 minutes or until a homogeneous mixture is formed. The antiperspirant active is then slowly added while mixing is continued. Mixing is then continued for an additional 10 minutes. Next the polyethylene powder is added slowly with mixing. After the addition is completed, mixing is continued for an additional 10 minutes. If fragrance is used it is added at this point and mixing is continued for an additional 5 minutes. The soft solid product is then transferred to suitable containers. This process may be done without the use of any added heat.

Example 3

General Method #3 of Making Compositions

The solvent components such as the volatile silicone (for example, cyclomethicone), emollients (such as non-volatile silicone (for example, phenyltrimethicone), C12–15 alkyl benzoate, neopentyl glycol diheptanoate and isopropyl myristate) are added to a large capacity mixer equipped with a mechanical stirrer and blended for about 5 minutes or until a homogeneous dispersion is formed. The antiperspirant active is then added as a dry powder with continuous mixing. This mixture is mixed for about 20 minutes or until a homogeneous dispersion is formed. The elastomer is then added and mixing is continued for about 10 minutes or until a homogeneous, white creamy paste is formed. At this point, the polyethylene beads are added and mixing is continued for another 20 minutes. If fragrance is to be added, it is done at this point and mixed until well blended or for about 5 minutes. The resulting soft solid is then pumped through a homogenizer (KINEMATIC—MT 61 Megatron unit homogenizer). Multiple passes through the homogenizer are used (usually about 1–4). It has been shown through experimentation that 4 passes are optimal for the stability of the final product to separation/syneresis. At 1–4 passes the product exhibits a syneresis of less than 8%, preferably less than 5% as evaluated by the process described in Example 5, below. The final product may be placed in suitable containers. No heating steps are required by this process. If, however, a component is used which requires melting, the premelting of this component will be required.

Example 4

General Method #4 of Making Compositions

When the elastomer content is in the low range of the composition and the fluids are of a percentage in the range of 18–23% by weight based on the total weight of the composition, the following process can be used. The cyclomethicone, dimethicone, neopentyl glycol diheptanoate, diethyl phthalate and isopropyl myristate are weighed separately and added sequentially to a properly sized stainless steel container. The ingredients are blended for about 5 minutes or until a homogeneous mixture is formed. The antiperspirant active is then slowly added while mixing is continued. Mixing can be done by an axial flow impeller with adequate power. Mixing is then continued for an additional 10 minutes. Next the polyethylene powder is added slowly with continued mixing. After the addition is completed, mixing is continued for an additional 10 minutes. This mixture is called the active phase. It is then added to a scraped wall mixing vessel with counter rotating blades (Lee, Agi or similar type) into which the formula amount of elastomer has already been charged. This is mixed for 20 minutes. If fragrance is used it is added at this point and mixing is continued for an additional 5 minutes. The soft solid product is then homogenized as described in Example 3. The product may then be transferred to suitable containers. This process may be done without the use of any added heat.

Example 5

Stability Evaluation

Samples (10.0 g) of formulated product are placed in a 25 cm$^3$ vial. The sample is incubated at a temperature of 50 degrees C. for 3 days and then centrifuged for 20 minutes at speed of 3900 rpm on a Centra CL2 centrifuge (from International Equipment Co., Needham Heights, Mass.). Any liquid remaining on top of the product sample was removed with a pipette and weighed. Percent syneresis is calculated as:

(weight of liquid removed after centrifugation)× 100/10.0

Normally it was desired to obtain syneresis levels of less than 8% and preferably less than 5% as described above. By way of comparison, the percent syneresis of a commercially available soft solid (Secret® Platinum powder fresh scent soft solid, a wax based product containing 19% aluminum zirconium trichlorohydrex gly (anhydrous), cyclopentasiloxane, dimethicone, tribehenin, C18–36 acid triglyceride and fragrance) exhibited a percent syneresis of about 19.79%.

Examples 6K, 6-K1, 6-N, and 6-O

The method described in Example 2 was done with the amounts of ingredients listed in TABLE A. The percent syneresis was measured by the method described in Example 5.

TABLE A

| Ingredient | Ex. 6K | Ex. 6-K1 | Ex. 6-N | Ex. 6-O |
| --- | --- | --- | --- | --- |
| Cyclomethicone and dimethicone crosspolymer (DC 9040) | 500.0 g (50.00%) | 250.00 g (50.00%) | 250.00 g (50.00%) | 260.00 g (52.00%) |
| Antiperspirant active (AZZ-902 SUF) | 250.0 g (25.00%) | 125.00 g (25.00%) | 125.00 g (25.00%) | 125.00 g (25.00%) |
| Neopentyl glycol diheptanoate | 0 | 25.00 g (5.00%) | 50.00 g (10.00%) | 25.00 g (5.00%) |
| Cyclomethicone (DC-245) | 95.0 g (9.50%) | 22.50 g (4.50%) | 0 | 22.50 g (4.50%) |
| Diethyl phthalate | 10.0 g (1%) | 5.00 g (1.00%) | 5.00 g (1.00%) | 5.00 g (1.00%) |
| Isopropyl myristate | 25.0 g (2.50%) | 12.50 g (2.50%) | 12.50 g (2.50%) | 12.50 g (2.50%) |

TABLE A-continued

| Ingredient | Ex. 6K | Ex. 6-K1 | Ex. 6-N | Ex. 6-O |
|---|---|---|---|---|
| Dimethicone DC-200 (1.5 centistokes) | 20.0 g (2.00%) | 10.00 g (2.00%) | 10.00 g (2.00%) | 10.00 g (2.00%) |
| Polyethylene (MICROTHENE FN 510) | 100.0 g (10.00%) | 45.00 g (9.00%) | 42.50 g (8.50%) | 35.00 g (7.00%) |
| Fragrance | 0 | 5.00 g (1.00%) | 5.00 g (1.00%) | 5.00 g (1.00%) |
| Total | 1000 g (100%) | 500.00 g (100%) | 500.00 g (100%) | 500.00 g (100%) |
| % Syneresis | 1.53 | 1.99 | 1.38 | 3.72 |

Range of elastomer content (solids basis) is 6–6.76% (upper and lower ranges calculated as 12%×50%–13%×52%) since solids content of DC-9040 is in the range of 12–13%.

Examples 6-P, 6-Q and 6-R

The method described in Example 2 was done with the amounts of ingredients listed in TABLE B. The percent syneresis was measured by the method described in Example 5.

TABLE B

| Ingredient | Ex. 6-P | Ex. 6-Q | Ex. 6-R |
|---|---|---|---|
| Cyclomethicone and dimethicone crosspolymer (DC-9040) | 250.00 g (50.00%) | 250.00 g (50.00%) | 250.00 g (50.00%) |
| Antiperspirant active (AZZ-902 SUF) | 125.00 g (25.00%) | 125.00 g (25.00%) | 125.00 g (25.00%) |
| Neopentyl glycol diheptanoate | 25.00 g (5.00%) | 25.00 g (5.00%) | 25.00 g (5.00%) |
| Cyclomethicone (DC-245) | 27.50 g (5.50%) | 35.00 g (7.00%) | 32.50 g (6.50) |
| Diethyl phthalate | 0 | 5.00 g (1.00%) | 5.00 g (1.00%) |
| Isopropyl myristate | 12.50 g (2.50%) | 0 | 12.50 g (2.50%) |
| Dimethicone DC-200 (1.5 centistokes) | 10.00 g (2.00%) | 10.00 g (2.00%) | 0 |
| Polyethylene (MICROTHENE FN 510) | 45.00 g (9.00%) | 45.00 g (9.00%) | 45.00 g (9.00%) |
| Fragrance | 5.00 g (1.00%) | 5.00 g (1.00%) | 5.00 g (1.00%) |
| Total | 500.00 g (100%) | 500.00 g (100%) | 500.00 g (100%) |
| % Syneresis | 3.15 | 4.16 | 3.75 |

Range of elastomer content (solids basis) is 6–6.5% (upper and lower ranges calculated as 12%×50%–13%×50%) since solids content of DC-9040 is in the range of 12–13%.

Examples 10–15

Examples of the invention may be made by using the method described in Example 3 with the amounts of ingredients listed in TABLE C. Note that for the elastomers, Crosspolymer A is a DC-9040 material obtained commercially and Crosspolymer B is a similar material which has been processed to a lower viscosity (75,000–250,000 cps) and a non-volatiles content of 9–12%).

TABLE C

| Ingredients (% by wt.) | Ex. 10 | Ex. 11 | Ex. 12 | Ex. 13 | Ex. 14 | Ex.15 |
|---|---|---|---|---|---|---|
| Neopentyl glycol diheptanoate | 3.00 | 3.00 | 3.00 | 3.00 | 1.00 | 1.00 |
| Cyclomethicone (DC-245) | 11.00 | 8.00 | 8.00 | 8.00 | 11.00 | 10.00 |
| Phenyl trimethicone (DC 556) | 1.00 | 1.00 | 1.00 | 1.00 | 1.00 | 1.00 |
| Isopropyl myristate | 1.00 | 1.00 | 1.00 | 1.00 |  | 1.00 |
| C12-15 alkyl benzoate | 5.00 | 5.00 | 5.00 | 5.00 | 5.00 | 5.00 |
| AlZr trichlorohydrex gly (Reach AZZ 902 SUF) | 25.00 | 25.00 | 25.00 | 25.00 | 25.00 | 25.00 |
| Polyethylene (Microthene FN 510) | 6.00 | 6.00 | 6.00 | 6.00 | 6.00 | 6.00 |
| Cyclomethicone and dimethicone crosspolymer ("A") | 47.00 | 10.00 | 7.50 | 5.00 | 10.00 | 10.00 |
| Cyclomethicone and dimethicone crosspolymer ("B") |  | 40.00 | 42.50 | 45.00 | 40.00 | 40.00 |
| Fragrance | 1.00 | 1.00 | 1.00 | 1.00 | 1.00 | 1.00 |
| Total | 100.00 | 100.00 | 100.00 | 100.00 | 100.00 | 100.00 |

Examples 16–20

Examples of the invention may be made by using the method described in Example 3 with the amounts of ingredients listed in TABLE D. Note that for the elastomers, DC-9040 material obtained commercially is used.

TABLE D

| Ingredients (% by wt.) | Ex. 16 | Ex. 17 | Ex. 18 | Ex. 19 | Ex. 20 |
|---|---|---|---|---|---|
| Neopentyl glycol diheptanoate | 1.00 | 3.00 | 1.00 | 1.00 | 3.00 |
| Cyclomethicone (DC-245) | 9.75 | 5.50 | 5.50 | 7.50 | 11.00 |
| Phenyl trimethicone (DC 556) | 1.00 | 1.00 | 1.00 | 1.00 | 1.00 |
| Isopropyl myristate | 1.00 | 1.00 | 1.00 | 1.00 | 1.00 |
| C12-15 alkyl benzoate | 5.00 | 5.00 | 7.00 | 5.00 | 5.00 |
| AlZr trichlorohydrex gly (Reach AZZ 902 SUF) | 25.00 | 25.00 | 25.00 | 25.00 | 25.00 |
| Polyethylene (Microthene FN 510) | 6.00 | 6.00 | 6.00 | 6.00 | 6.00 |
| Cyclomethicone and dimethicone crosspolymer | 50.00 | 52.50 | 52.50 | 52.50 | 47.00 |
| Aloe Vera, Powder (Veragel 200 standardized) | 0.05 | | | | |
| Fragrance | 1.20 | 1.00 | 1.00 | 1.00 | 1.00 |
| Total | 100.00 | 100.00 | 100.00 | 100.00 | 100.00 |

Range of elastomer content (solids basis) is 5.64–6.825% (upper and lower ranges calculated as 12%×47%–13%×52.5%) since solids content of DC-9040 is in the range of 12–13%.

Examples 21–24

Examples of the invention may be made by using the method described in Example 3 with the amounts of ingredients listed in TABLE E. Note that for the elastomers, DC-9040 material obtained commercially is used.

TABLE E

| Ingredients (% by wt.) | Ex. 21 | Ex. 22 | Ex. 23 | Ex. 24 |
|---|---|---|---|---|
| Neopentyl glycol diheptanoate | | | 1.00 | 0.50 |
| Cyclomethicone (DC-245) | 8.25 | 5.25 | 5.25 | 6.75 |
| Phenyl trimethicone (DC 556) | | | 1.00 | 0.50 |
| Isopropyl myristate | | | 1.00 | 0.50 |
| C12-15 alkyl benzoate | 7.00 | 7.00 | 7.00 | 7.00 |
| PPG-3 myristyl ether | | 3.00 | | |
| AlZr trichlorohydrex gly (Reach AZZ 902 SUF) | 25.00 | 25.00 | 25.00 | 25.00 |
| Polyethylene (Microthene FN 510) | 6.00 | 6.00 | 6.00 | 6.00 |
| Cyclomethicone and dimethicone crosspolymer | 52.50 | 52.50 | 52.50 | 52.50 |
| Aloe Vera, Powder (Veragel 200 standardized) | 0.05 | 0.05 | 0.05 | 0.05 |
| Fragrance | 1.20 | 1.20 | 1.20 | 1.20 |
| Total | 100.00 | 100.00 | 100.00 | 100.00 |

We claim:

1. A low residue antiperspirant and/or deodorant composition comprising:
   (a) 40–75% of a volatile silicone;
   (b) 5–15% of an emollient;
   (c) 1–10% on a solids basis of a cyclomethicone (and) dimethicone crosspolymer made with an ≡Si—H containing polysiloxane and an alpha, omega-diene of formula $CH_2=CH(CH_2)_xCH=CH_2$, where x=1–20, to form a gel by crosslinking and addition of ≡Si—H across double bonds in the alpha, omega diene, which crosspolymer has a viscosity in the range of 50,000–3,000,000 centipoise and a nonvolatiles content of 10–14% in cyclomethicone;
   (d) 0.1–20% of an antiperspirant active based on an anhydrous, buffer-free basis; and
   (e) 2–10% of polyethylene beads having a particle size in the range of 5–40 microns and a density in the range of 0.91–0.98 g/cm$^3$;
   wherein the composition is an anhydrous, surfactant-free and antiseptic alcohol-free soft solid form exhibiting a syneresis of less than 8%.

2. An antiperspirant and/or deodorant composition according to claim 1 comprising 6.00–6.76% (on a solids basis) of the cyclomethicone (and) dimethicone crosspolymer.

3. An antiperspirant and/or deodorant composition according to claim 1 comprising 5.64–6.82% (on a solids basis) of the cyclomethicone (and) dimethicone crosspolymer.

4. An antiperspirant and/or deodorant composition according to any one of claim 1, 2 or 3 wherein the volatile silicone is cyclomethicone.

5. An antiperspirant and/or deodorant composition according to any one of claim 1, 2 or 3 wherein the emollient comprises one or more members selected from the group consisting of
   (a) fats and oils which are the glyceryl esters of fatty acids or triglycerides of Formula III:

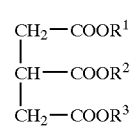

Formula III wherein each of $R^1$, $R^2$, and $R^3$ maybe the same or different and have a carbon chain length (saturated or unsaturated) of 7 to 30;
   (b) hydrocarbons;
   (c) esters of formula $R^4CO$—$OR^5$, wherein the chain length for each of $R^4$ and $R^5$ is from 7 to 30 and can be saturated or unsaturated, straight chained or branched;

(d) saturated and unsaturated fatty acids having a formula $R^6COOH$ wherein $R^6$ has a carbon chain length from 7 to 30 and can be straight or branched chain;
(e) saturated and unsaturated fatty alcohols having a formula $R^7CH_2OH$ wherein $R^7$ has a carbon chain length from 7 to 30 and can be straight or branched chain;
(f) lanolin and its derivatives;
(g) alkoxylated alcohols wherein the alcohol portion is selected from the group consisting of aliphatic alcohols having a carbon chain length from 2 to 18, and the alkylene portion is selected from the group consisting of ethylene oxide, and propylene oxide having a number of alkylene oxide units from 2 to 53;
(h) silicones and silanes which are members of the group consisting of polymers of silicon/oxygen having general structures:
  (1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl;
  (2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl; or
  (3) organo substituted silicon compounds of formula $R^{17}Si(R^{18})OSiR^{19}$ which are not polymeric where $R^{17}$, $R^{18}$ and $R^{19}$ can be the same or different and are each independently selected from the group consisting of phenyl and C1–C60 alkyl optionally with one or both of the terminal R groups also containing an hydroxyl group; and
(i) mixtures and blends of two or more of (a)–(h).

6. An antiperspirant and/or deodorant composition according to any one of claim 1, 2 or 3 comprising an emollient as one or more members selected from the group consisting of dimethicone, dimethiconol behenate, $C_{30-45}$ alkyl methicone, stearoxytrimethylsilane, phenyl trimethicone and stearyl dimethicone.

7. An antiperspirant and/or deodorant composition according to claim 1 comprising 45–60% of the volatile silicone.

8. An antiperspirant and/or deodorant composition according to claim 1 comprising 2–8% of the polyethylene beads.

9. An antiperspirant and/or deodorant composition according to claim 1 comprising 10–20% of the antiperspirant active.

10. An antiperspirant/deodorant composition according to any one of claim 1, 2 or 3 which comprises:
 (a) an emollient selected from the group consisting of 1–8% C12–15 alkyl benzoate; 0.5–5% neopentyl glycol diheptanoate; 0.5–2% isopropyl myristate; and 0.4–1.5% phenyltrimethicone; and
 (b) 15–20% antiperspirant active.

11. An antiperspirant/deodorant composition according to any one of claim 1, 2 or 3 which comprises:
 (a) an emollient selected from the group consisting of 1–8% C12–15 alkyl benzoate; 0.3–5% neopentyl glycol diheptanoate; 0.3–2% isopropyl myristate; and 0.3–1.5% phenyltrimethicone; and
 (b) 15–20% antiperspirant active.

12. An antiperspirant and/or deodorant composition according to any one of claim 1, 2, 3, 7, 8 or 9 wherein the amount of syneresis does not exceed 5%.

* * * * *